US00PP11832P2

(12) United States Plant Patent

Jessel, Jr.

(10) Patent No.: US PP11,832 P2
(45) Date of Patent: Apr. 3, 2001

(54) CARNATION PLANT NAMED 'CFPC AMANTE'

(75) Inventor: Walter H. Jessel, Jr., Gonzales, CA (US)

(73) Assignee: California Florida Pland Co, LP, Salinas, CA (US)

( * ) Notice: Subject to any disclaimer, the term of this patent is extended or adjusted under 35 U.S.C. 154(b) by 0 days.

(21) Appl. No.: 09/181,276

(22) Filed: Oct. 28, 1998

(51) Int. Cl.[7] ..... A01H 5/00
(52) U.S. Cl. ..... Plt./276
(58) Field of Search ..... Plt./276, 273, 277, Plt./272, 281, 282

*Primary Examiner*—Bruce R. Campell
*Assistant Examiner*—Michelle Kizilkaya
(74) *Attorney, Agent, or Firm*—Christie, Parker & Hale, LLP

(57) ABSTRACT

A new variety of carnation plant producing medium pink flowers.

1 Drawing Sheet

BACKGROUND OF THE INVENTION

The present invention relates to a new and distinct variety of carnation plant which was discovered by me as a natural branch mutation in a controlled planting of 'CFPC Passion' (U.S. Plant Pat. No. 10,416). The varietal denomination of the new variety is 'CFPC Amante'.

SUMMARY OF THE INVENTION

Among the novel characteristics possessed by the new variety which distinguishes it is flowers of medium pink coloration that retain color without fading. When grown under glass in Salinas, Calif., pinched plants grown in 4½ inch plastic pots are about 7¾ inches tall and about 7 inches wide (average). Flower diameter averages about 2 inches with a crown of about ¾ inch. Foliage is about 3½ inches long and about 5/16 inches wide.

Asexual reproduction by propagation by side shoot cuttings of the new variety as performed in Salinas, Calif., shows that the foregoing and other distinguishing characteristics come true to form and are established and transmitted through succeeding propagations.

COMPARISON WITH PARENT

The new variety differs from its parent 'CFPC Passion', U.S. Plant Pat. No. 10,416, in having different flower color.

BRIEF DESCRIPTION OF ILLUSTRATION

The accompanying illustration shows typical specimens of the vegetative growth and flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Phenotypical expression may vary depending upon varying environmental, seasonal and cultural conditions.

The information provided herein is based on observations of plants grown inside commercial greenhouses at Salinas, Calif. The height of plant and flower and foliage size are established as an average using standard commercial cultural practices.

Classification:
*Botanical.*—*Dianthus caryophyllus.*
*Commercial.*—Carnation, greenhouse type, suitable for production as a pot spray.
Parentage: Sport of 'CFPC Passion'.

1. Plant:
*Height.*—About 7¾ inches.
*Growing habit.*—Herbaceous, semi-upright.
*Blooming habit.*—As a spray (pot).
*Blooming season.*—Year round.
*Breaking action.*—Good, 10–11 per plant, pinching is required for good breaking action.
*Rooting time.*—About 18 days.
*Disease resistance.*—Good, typical for carnations.

2. Foliage:
*Color.*—Upper side: Near 137A. Lower side: Near 137B.
*Size.*—About 3½ inches long, about 5/16 inches wide.
*Quantity.*—Numerous.
*Shape.*—Lanceolate.
*Texture.*—Smooth.
*Ribs.*—Central keeled.
*Arrangement.*—Bi-lateral along stem.
*Stem color.*—Near 135B.

3. Bud:
*Shape.*—Ovoid.
*Color.*—Near 138B.
*Length.*—About 1 3/16 inches.
*Diameter.*—About 7/16 inch.

4. Calyx:
*Number of bracts.*—About 5, near 147A.
*Length.*—About ¼ inch.
*Width.*—About 3/16 inch.
*Color.*—Outside — near 138B. Inside — near 145C.
*Bursting/Splitting.*—Has not been observed.

5. Bloom:
   *Shape.*—Round.
   *Size.*—Diameter average: About 2 inches. Depth average: About ¾ inch.
   *Borne.*—As a spray of about 2 to 3 blooms per spray.
   *Color.*—When blooms open, color appears darker in comparison to fully open bloom, color tends to fade to lighter color as blooms fully open. General tonality: Medium pink. Upper side: Near 63C. Lower side: Near 63D. Center: Near 63C. Pedicel: Near 147A. Outer petals: Near 63C.
   *Fragrance.*—None to slight.
6. Petals:
   *Number.*—About 16.
   *Outer petals.*—Length; About 1⅔ inches. Width: About 13/16 inch.
   *Central petals.*—Length: About 1⅓ inches. Width: About ¾ inch.
   *Texture.*—Smooth.
   *Form.*—Fan shaped.
   *Appearance.*—Shiny.
   *Margin.*—Smooth.
   *Lastingness of flower.*—Up to about 1 week after cutting.
7. Reproductive organs:
   *Stamens.*—None.
   *Pistil.*—Number: 1. Color: Whiter than 155D. Length About 1 inch.
   *Stigma.*—Number: About 3. Color: Whiter than 155D.
   *Ovary.*—Shape: Conical. Color: Base — near 11D. Body — near 144A. Apex — near 144A.
   *Fertility.*—Female: Good. Male: None.

I claim:

1. A new and distinct carnation plant of the variety substantially as shown and described.

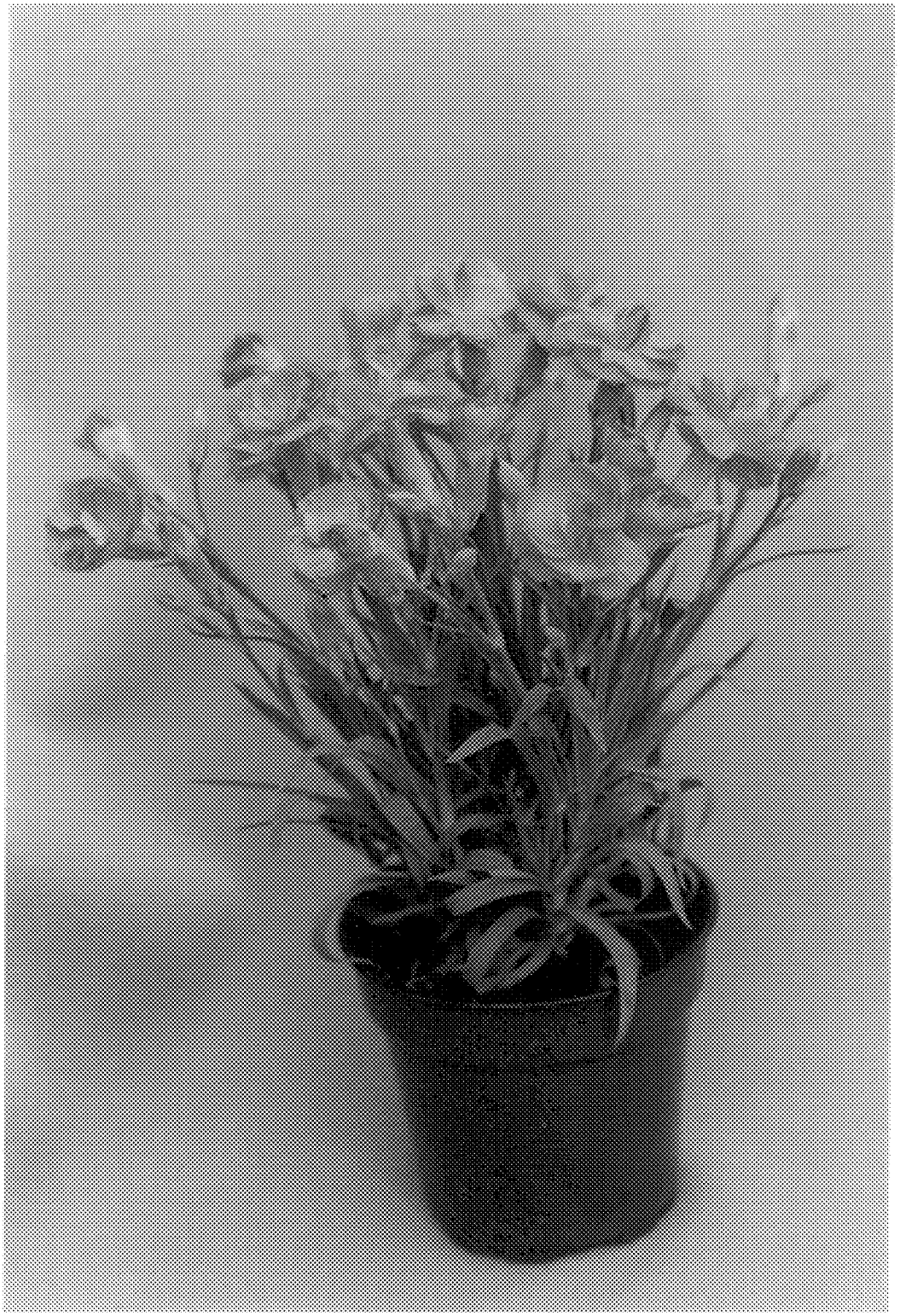

* * * * *